US00PP16676P2

(12) United States Plant Patent
Utecht

(10) Patent No.: US PP16,676 P2
(45) Date of Patent: Jun. 20, 2006

(54) *GERANIUM* PLANT NAMED 'FISTUFRU'

(50) Latin Name: *Pelargonium peltatum*
Varietal Denomination: Fistufru

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 90 days.

(21) Appl. No.: 10/998,656

(22) Filed: Nov. 30, 2004

(51) Int. Cl.
*A01H 5/00* (2006.01)

(52) U.S. Cl. ..... Plt./332

(58) Field of Classification Search ..... Plt./332
See application file for complete search history.

(56) References Cited

PUBLICATIONS

German PBR Application No. PEL 1894 filed Jun. 4, 2003 (Copy of German Gazette dated 1) Jul. 15, 2003—Listing Assigned Application for Protection Number (2 pp.). and 2) May 15, 2004—Publishing Proposed Variety Denomination (2 pp.)).

Canadian PBR Application No. 03–3898 filed Nov. 21, 2003 (Copy of a Candian Plant Varieties Journal dated Jan., 2004 Listing Assigned Application Number (2 pp.).

*Primary Examiner*—Kent Bell
(74) *Attorney, Agent, or Firm*—Foley & Lardner LLP

(57) ABSTRACT

A new and distinct cultivar of *geranium* plant named 'Fistufru', particularly characterized by the combined features of rose-red, open flowers, with deep-red macules on petals; almost single-type flowers on long peduncles; medium green foliage with weak, narrow zonation; moderately vigorous plant growth; initially round and bushy, and later, long trailing plant habit; and mid-spring season flowering response.

1 Drawing Sheet

Genus and species of the plant claimed: *Pelargonium peltatum* L'Héritier (hybrid).
Variety denomination: 'Fistufru'.

BACKGROUND OF THE INVENTION

The present invention comprises a new and distinct cultivar of *geranium*, botanically known as *Pelargonium peltatum*, and hereinafter referred to by the cultivar name 'Fistufru'.

'Fistufru' is a product of a planned breeding program which had the objective of creating new ivy *geranium* cultivars with semi-double to double-type flowers, zoned foliage, and about medium sized, well-branched growth habit, in various flower colors.

'Fistufru' originated from a hybridization made by the inventor, Angelika Utecht, in a controlled breeding program in Hillscheid, Germany, in 1999. The female parent of 'Fistufru' was the patented variety 'Fisam' (U.S. Plant Pat. No. 8,327), and is described as having light violet, double flowers, medium green foliage with strong zonation, and moderately vigorous growth habit. The male parent of 'Fistufru' was the unpatented plant No. 93-361-3, which was characterized by red, semi-double flowers, foliage with weak zonation, and relatively tall plant habit.

'Fistufru' was selected as one flowering plant within the progeny of the stated cross by Angelika Utecht in 2000 in a controlled environment in Fuerteventura, Canary Islands, Spain.

The first act of asexual reproduction of 'Fistufru' was accomplished when vegetative cuttings were taken from the initial selection in the fall of 2000 in a controlled environment in Fuerteventura, Canary Islands, Spain, by, or under the supervision of, Angelika Utecht.

Horticultural examination of plants grown from cuttings of the plant initiated in May of 2001 in Hillscheid, Germany, and continuing thereafter, has demonstrated that the combination of characteristics as herein disclosed for 'Fistufru' are firmly fixed and are retained through sucessive generations of asexual reproduction.

BRIEF SUMMARY OF THE INVENTION

'Fistufru' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fistufru' in combination distinguish this *geranium* as a new and distinct cultivar:

1. rose-red flowers with large, deep-red macules on upper petals;
2. almost single-type flowers on long peduncles;
3. medium green foliage with weak zonation;
4. moderately vigorous growth, trailing plant habit;
5. about mid-spring flowering response; and
6. good weather resistance of the flowers.

Of the many commercial cultivars known to the present inventor, there is no cultivar very close in comparison. However, 'Fistufru' might be compared with 'Fisdream' (U.S. Plant Pat. No. 14,920).

In comparison to 'Fisdream', 'Fistufru' has flowers of a roughly similar overall color, but there are dark-red flares on petals, and generally fewer petals per flower. Furthermore, 'Fistufru' does not grow quite as vigorously.

BRIEF DESCRIPTION OF THE DRAWINGS

The accompanying photographic drawing shows typical flower and foliage characteristics of 'Fistufru' with colors being as true as possible with an illustration of this type. The photographic drawing shows a side perspective view of a flowering potted plant of 'Fistufru' with leaves, buds and infloresences.

DETAILED BOTANICAL DESCRIPTION

The measurements were taken in Hillscheid, Germany, in mid May 2003, 15 weeks after planning of rooted cuttings. The plants were growing in 14 cm pots; they had been pinched once.

In the following description color references are made to The Royal Horticultural Society Color Chart. The color values were determined indoors from plants growing in a green-house in May 2003, in Hillsheid, Germany.

Parentage:
- *Male parent.*—Unpatented, hybrid plant No. 93-361-3.
- *Female parent.*—'Fisam' (U.S. Plant Pat. No. 8,327).

Classification: *Pelargonium peltatum* L'Héritier (hybrid).
Propagation: Vegetative cuttings.
Inflorescence:
Umbel:
- *Shape.*—Irregular to incompletely semi-spherical.
- *Average diameter.*—87 mm.
- *Average depth.*—50–55 mm.

Peduncle:
- *Peduncle length.*—136 mm.
- *Peduncle diameter.*—3 mm.
- *Peduncle color.*—Light green, RHS 143 C.

Pedicel:
- *Pedicel length.*—33 mm in length, usually with a spur near the base of the flower.
- *Pedicel diameter.*—2 mm.
- *Pedicel color.*—Mainly dark greyed-purple, RHS 187 C.
- *Number of flowers per umbel.*—About 8–11.

Corolla:
- *Average length.*—54 mm.
- *Average width.*—49 mm.
- *Form.*—Semi-double type, often appearing as single-type.
- *Shape.*—Appearing almost round, but actually weakly zygomorphic, often with a gap between the upper and lower petals.

Petaloids:
- *Number of petaloids.*—0–2 .
- *Length.*—Variable, maxium length (about half the length of the petals): up to about 15 mm.
- *Width.*—Variable, from 2 mm and up to 7 mm.
- *Overall shape.*—Variable, mostly narrow, filament-like, some are nearly petal-shape, but distinctly smaller and often curled or 'deformed'.
- *Apex shape.*—Acute or rounded.
- *Base shape.*—Acute or attenuate.
- *Margin.*—Unable to ascertain.
- *Color of upper petaloids.*—Red, either RHS 55 A or RHS 52 A; lower part nearly white, RHD 56 D.
- *Color of lower petaloids.*—From nearly white, RHS 56 D, to RHS 55 A (pink).

Petals:
- *Number of petals.*—5–7.
- *Shape of petals.*—Obovate, base attenuate, upper end is rounded, margin is entire.
- *Size of petals.*—Upper petals: 35 mm long, 25 mm wide. Lower petals: 28–29 mm long, 22 mm wide.
- *Color (general tonality from a distance of three meters).*—Rose-red to purple-pink.
- *Color of upper petals.*—Near margin, red-purple, RHS N57 B; large flare in the middle of petals: deep red, between RHS 46 B to red-purple, RHS N57 A.
- *Markings of upper petals.*—2 dark-greyed purple veins, RHS N187 B.
- *Color of lower petals.*—Red-purple, RHS 57 B to 57 C.
- *Markings of lower petals.*—Red macules, RHS 46 B, weaker and less distinct than with upper petals.
- *Color of lower surface of petals.*—Red-purple, approximately RHS 58 B to 58 C.

Sepals:
- *Number of sepals.*—5 .
- *Shape of sepals.*—Linear to lanceolate, acute tip, fused base, surface with weak pubescence, margin entire.
- *Size of sepals.*—17 mm long, 6–7 mm wide for the largest upper sepal, 3–4 mm in width for the other sepals.
- *Color of sepal.*—Both surfaces: yellow-green, mainly RHS 146 C, near tips green, RHS 143 C, largest sepal: greyed-purple RHS 185 A for the lower surface, greyed-purple, RHS 184 A for the upper surface.

Bud: (Just prior to petals unfolding).
- *Shape.*—Narrow, elliptical.
- *Color of sepals.*—Light green, RHS 143 C.
- *Color of petals.*—Red, RHS 46 B to 46 C.
- *Length.*—23 mm.
- *Width.*—11 mm.

Reproductive organs:
- *Androecium.*—7 fertile anthers, plenty pollen, orange, RHS N25 A, filaments white, RHS 155 D, to light-pink, RHS 52 D.
- *Gynoecium.*—One pistil, whitish style, RHS 155 D to red-purple, N66D, stigma 5–6-lobed, dark greyed-purple, RHS 187 B.
- *Fertility/seed set.*—Only few, mainly from late summer to fall.
- *Fruit.*—Oblong, about 5–6 mm wide, rostrum (beak) 38–42 mm long.
- *Seed.*—Oblong, 4–5 mm long, greyed-orange, RHS 177 B.

Spring flowering response period: In Hillscheid, Germany, in 2003 plants had on average 0.5 flowers opened 12 weeks after planting of rooted cuttings (pinched plants).

Outdoor flower production: Continuously and moderately rich flowering, the flower count in 2003 in Hillscheid, Germany, indicated about 20–25 inflorescence per plant in late summer.

Durability: Good stability of flower color, practically no shattering (dropping of petals), good rain resistance due to the open flower type with relatively few petals.

Lastingness of the individual flower: About 10 days at 18° C.

Fragrance: None.

Plant:

Foliage:
- *Overall shape.*—Ivy-shaped, with distinct lobes.
- *Base shape.*—Cordate base, with the gap at the base nearly closed, the lowest lobes are partly overlapping.

*Apex shape.*—Rounded apex with distinct lobes.
*Margin.*—Entire.
*Texture.*—Upper surface smooth, flat, glossy.
*Size of leaf.*—80 mm wide, about 50 mm long.
*Color of upper surface.*—Medium green, closest to RHS 137 C.
*Color of zonation.*—Greyed orange, closest to RHS 166 A, forming a narrow ring; distinctness: weak to medium.
*Color of lower surface.*—Green, RHS 143 A.
*Petiole.*—38 mm long, 2 mm diameter, green in color, closest to RHS 143 B.

General appearance and form:
*Stem color.*—Light green, RHS 143 B.
*Internode length.*—25–35 mm.
*Branching pattern.*—8.5 branches on average.
*Size of plants.*—Growth form: Decumbent, when young somewhat ascending, later overhanging and trailing (plant shape therefore depending on the shape and size of the container/basket used). Height: 15.5 cm (15 week-old plants, as described). Diameter: 24 cm (15 week-old plants, as described). Length: 16 cm (15 week old plants, as described). 87 cm (30 week-old plants, around September 1), measured from the top of the soil (base of the main stem) to the tips of the branches, without inflorescences.

I claim:

1. A new and distinct cultivar of *geranium* plant named 'Fistufru', as described and illustrated herein.

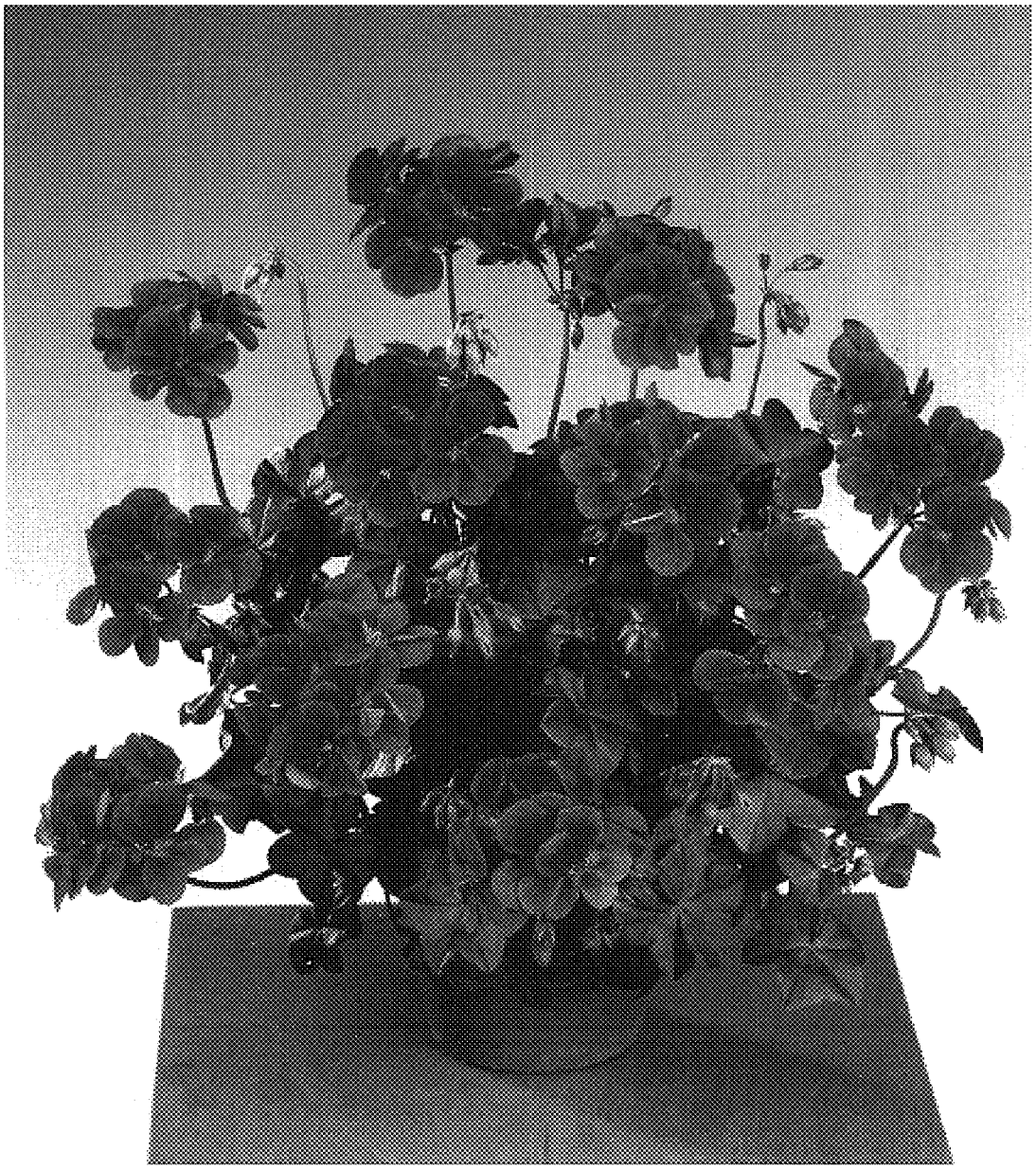

* * * * *